(12) United States Patent
Baumfalk et al.

(10) Patent No.: US 9,103,703 B2
(45) Date of Patent: Aug. 11, 2015

(54) CONTAINER HAVING A SENSOR ADAPTER

(75) Inventors: Reinhard Baumfalk, Goettingen (DE);
Wolfgang Kahlert, Koerle (DE);
Gerhard Greller, Goettingen (DE)

(73) Assignee: Sartorius Stedim Biotech GmbH (DE)

( * ) Notice: Subject to any disclaimer, the term of this patent is extended or adjusted under 35 U.S.C. 154(b) by 0 days.

(21) Appl. No.: 13/376,454

(22) PCT Filed: May 7, 2010

(86) PCT No.: PCT/EP2010/002808
§ 371 (c)(1),
(2), (4) Date: Dec. 6, 2011

(87) PCT Pub. No.: WO2010/145735
PCT Pub. Date: Dec. 23, 2010

(65) Prior Publication Data
US 2012/0097557 A1    Apr. 26, 2012

(30) Foreign Application Priority Data

Jun. 16, 2009  (DE) .......................... 10 2009 025 419
Aug. 14, 2009  (DE) .......................... 10 2009 037 345

(51) Int. Cl.
| | | |
|---|---|---|
| *G01D 21/00* | (2006.01) | |
| *G01D 11/30* | (2006.01) | |
| *C21C 5/52* | (2006.01) | |
| *C21C 5/56* | (2006.01) | |
| *C22B 1/00* | (2006.01) | |
| *C22B 7/00* | (2006.01) | |
| *C22B 19/30* | (2006.01) | |

(52) U.S. Cl.
CPC ................ *G01D 11/30* (2013.01); *C21C 5/527* (2013.01); *C21C 5/565* (2013.01); *C22B 1/005* (2013.01); *C22B 7/006* (2013.01); *C22B 19/30* (2013.01)

(58) Field of Classification Search
None
See application file for complete search history.

(56) References Cited

U.S. PATENT DOCUMENTS 2,861,710 A  *  11/1958  Thompson .................... 220/265
4,003,709 A       1/1977  Eaton et al.
4,404,284 A  *   9/1983  Heider et al. .............. 435/287.1

(Continued)

FOREIGN PATENT DOCUMENTS

DE    10 2006 001 610    7/2007
DE    10 2006 022 307    11/2007

(Continued)

OTHER PUBLICATIONS

International Preliminary Report, Dec. 2011.

(Continued)

*Primary Examiner* — Robert R Raevis
(74) *Attorney, Agent, or Firm* — Gerald E. Hespos; Michael J. Porco; Matthew T. Hespos

(57) ABSTRACT

A container having a sensor adapter for receiving a sensor arrangement for measuring at least one parameter of media contained in a container interior, wherein the sensor adapter is arranged on the wall to the container interior and has an externally accessible receiving opening in a receiving channel, which is bounded toward the container interior, for adapting the sensor arrangement, wherein toward the container interior the receiving channel in the sensor adapter has at least one boundary surface which is formed by a membrane and via which the medium or media to be measured can be supplied to the sensor arrangement.

17 Claims, 4 Drawing Sheets

(56) References Cited

U.S. PATENT DOCUMENTS

| | | | |
|---|---|---|---|
| 4,695,551 A * | 9/1987 | Samhaber et al. | 435/309.2 |
| 6,131,473 A * | 10/2000 | Hoffman et al. | 73/866.5 |
| 6,197,172 B1 | 3/2001 | Dicks et al. | |
| 6,225,108 B1 | 5/2001 | Larsen et al. | |
| 6,658,940 B2 * | 12/2003 | Burczyk et al. | 73/715 |
| 2003/0228684 A1 * | 12/2003 | Burbidge et al. | 435/292.1 |
| 2005/0042133 A1 * | 2/2005 | Staphanos | 422/50 |
| 2007/0185472 A1 | 8/2007 | Baumfalk et al. | |
| 2009/0139298 A1 * | 6/2009 | Klees et al. | 73/1.03 |
| 2010/0065013 A1 | 3/2010 | Weber et al. | |
| 2010/0255526 A1 * | 10/2010 | Braet et al. | 435/29 |
| 2011/0111489 A1 * | 5/2011 | Beese et al. | 435/289.1 |
| 2011/0226039 A1 * | 9/2011 | Roland et al. | 73/23.31 |
| 2013/0256308 A1 * | 10/2013 | Perry et al. | 220/214 |

FOREIGN PATENT DOCUMENTS

| | | |
|---|---|---|
| EP | 0372121 | 6/1990 |
| WO | 93/15402 | 8/1993 |
| WO | 2006/017951 | 2/2006 |
| WO | 2008/071022 | 6/2008 |

OTHER PUBLICATIONS

European Patent Application No. 2 443 420-Office Action issued May 11, 2015.

* cited by examiner

CONTAINER HAVING A SENSOR ADAPTER

BACKGROUND OF THE INVENTION

1. Field of the Invention

The invention relates to a container having a sensor adapter for receiving a sensor arrangement for measuring at least one parameter of media contained in a container interior, wherein the sensor adapter is arranged on the wall to the container interior and has an externally accessible receiving opening in a receiving channel, which is bounded toward the container interior, for adapting the sensor arrangement.

2. Description of the Related Art

DE 10 2006 001 610 B4 discloses a bioreactor or container which is formed in particular as a disposable mixing bag and has a sensor adapter for receiving a sensor arrangement in the form of an optical sensor, which is formed by one end of a light conductor and is fitted in a reversible manner. The sensor adapter, which is arranged in the wall to the reactor interior, has an externally accessible receiving opening in a receiving channel, which is bounded toward the reactor interior by a transparent material.

The disadvantage of the known sensor adapter is that it is suitable only for optical measuring operations. The sensor adapter is not suitable for the installation of conventional reversible electrodes or sensor arrangements for measuring the pH, the carbon dioxide or oxygen content or for measuring the conductivity. The known adapters are also not suitable for the use of gas sensors, as are known for dissolved oxygen or dissolved carbon dioxide.

Furthermore, sensor adapters are known from DE 10 2006 022 307 A1 and from WO 2006/017951 A1, said sensor adapters likewise having the abovementioned disadvantages.

If in particular gas sensors are intended to be used, the known adapters either have to use permanently installed sensors, which are not reversible and are also susceptible to a need for sterilization, or the adapters have to be open toward the reactor interior. If the adapters are open toward the reactor interior, it is possible to use exchangeable gas sensors, but these likewise have to be sterilized, which is associated with problems.

Containers in the context of the present invention are understood to mean in particular containers for mixing, storing and transporting, and also bioreactors and fermenters. The containers can be made in particular of plastics material.

In the context of the present invention, media are considered to be in particular liquids, gases, suspensions, dispersions, buffers and cell culture broths.

Parameters are understood in the following text to mean in particular concentrations of substances, pressure or partial pressure of gases (oxygen, carbon dioxide), moisture, the number of particles, turbidity, temperature, pH, electromagnetic rays, fluorescence, electrical conductivity, and also capacitive and electrical resistances.

It is therefore the object of the present invention to develop the known containers having a sensor adapter in such a way that it is possible to use sensor arrangements which require contact with the media to be measured, for example gas sensors.

SUMMARY OF THE INVENTION

The invention relates to a container having a sensor adapter for receiving a sensor arrangement for measuring at least one parameter of media in the container. The sensor adapter is arranged on a wall of the container and has an externally accessible receiving opening in a receiving channel. The receiving channel in the sensor adapter has at least one boundary surface which is formed by a membrane and via which the medium or media to be measured can be supplied to the sensor arrangement.

On account of the configuration of at least a part of the boundary surface to the reactor interior as a membrane, it is possible for the medium to be measured to come into direct contact with the sensors of the sensor arrangement. At the same time, by way of the membrane, contamination of the reactor interior by the sensor arrangement or the sensors thereof is avoided. The sensor arrangement having sensitive sensors does not have to be sterilized, but rather only the sensor adapter fastened to the bioreactor.

According to a preferred embodiment of the invention, the membranes have a pore size of between 0.1 and 0.4 $\mu$m, preferably of $\leq$0.2 $\mu$m. Thus, the membranes form a sterile barrier between the reactor interior and the reversibly attachable sensor arrangement.

According to a further preferred embodiment of the invention, the membrane has hydrophilic, hydrophobic or oleophobic properties, depending on the contacted medium. Depending on the configuration of the sensor adapter, it is possible for example for the first membrane to dip into the liquid medium located in the reactor interior, while for example the second membrane is arranged in the top space of the reactor interior and makes contact with the gas phase. Depending on the contacted medium, it is then expedient to configure the membrane in a hydrophilic or hydrophobic manner. In any case, the sensor adapter should be relatively free of germs.

According to a further preferred embodiment of the invention, the membrane has one or more regions having hydrophilic properties and one or more regions having hydrophobic properties. For example, the membrane is configured as a hydrophilic membrane having a plurality of hydrophobic spots or as a hydrophobic membrane having a plurality of hydrophilic spots. Thus, when the sensor arrangement is advanced over the hydrophobic regions of the membrane, gas can be pressed in a sterile manner into the container interior. Liquid medium from the container interior can pass through the hydrophilic regions of the membrane and flow around the sensor of the sensor arrangement.

According to a further preferred embodiment of the invention, the membrane is made of a natural polymer, such as cellulose acetate or regenerated cellulose, for example.

According to a further embodiment of the invention, the membrane is made of a synthetic polymer, such as polysulfone, for example.

According to a further preferred embodiment of the invention, the receiving channel forms an adapter shaft projecting into the container interior, said adapter shaft having two successively arranged membranes, which have different properties, and having a closed end side.

According to a further preferred embodiment of the invention, the receiving channel forms an adapter shaft projecting into the container interior, said adapter shaft having a first membrane which closes its end side, and having a second membrane which is arranged on its perimeter and has different properties than the first membrane. However, the receiving channel may also form an adapter shaft projecting into the container interior, said adapter shaft having a first membrane arranged on its perimeter, having a closed end side and having a side channel which leads outward and the access opening of which, which is located outside the reactor interior, is likewise covered by a membrane or by a filter element that has a membrane. The second membrane may in this case likewise have hydrophilic, hydrophobic or other properties. The side channel which leads outward is suitable in particular for obtaining cell-free liquid which can be supplied to an analyzer.

According to a further preferred embodiment of the invention, the sensor arrangement is arranged in the form of a plunger in the receiving channel such that it can be moved longitudinally in order to generate a pressure. In this case, the ability to be moved longitudinally can be achieved for example by way of a bellows, via which the sensor arrangement which is arranged in the receiving channel is connected to the sensor adapter.

According to a further preferred embodiment of the invention, the sensor adapter is made of a material that is resistant to beta radiation and/or to gamma radiation and/or to ethylene oxide (ETO). Thus, the sensor adapter is suitable to be sterilized together with the disposable bioreactor.

The sensor adapter may be arranged for example in a side wall or in the top region of the container. Thus, it is possible to install it at the level of the liquid in the reactor interior or to install it in the top space. The membrane may be in contact with the liquid media but may also be in contact with the gas phase in the top space.

Of course, the sensor adapter has to be adapted in each case to the sensor arrangement provided.

According to a further preferred embodiment of the invention, the container is in the form of a disposable bioreactor.

Further details of the invention can be gathered from the following detailed description and from the appended drawings, in which preferred embodiments of the invention are illustrated by way of example.

DETAILED DESCRIPTION OF THE PREFERRED EMBODIMENTS

A container 2, which is configured in the exemplary embodiment as a disposable bioreactor 1, consists substantially of the container 2 and a sensor adapter 3.

Figure 1:
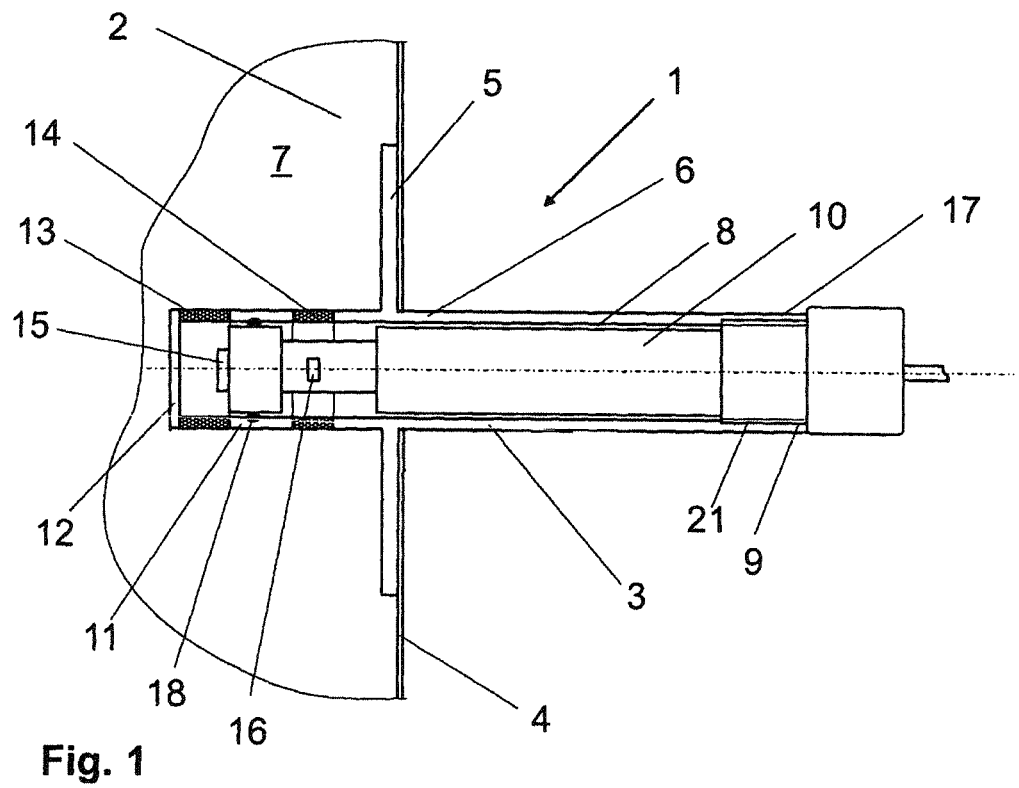
FIG. 1 shows a schematic side view of a container in outline, with a sensor adapter in section and an unsectioned sensor arrangement.

In the exemplary embodiment in FIG. 1, the container 2 is in the form of a foldable, flexible bag, in the wall 4 of which the sensor adapter 3 is arranged. The sensor adapter 3 has a flange 5, which is welded to the wall 4. The sensor adapter 3 has an adapter shaft 6, which projects from outside the container 2, through the wall 4 and into the reactor interior 7. Centrally, the sensor adapter 3, or its adapter shaft 6, has a receiving channel having an externally accessible receiving opening 9. Via the receiving opening 9, a sensor arrangement for measuring a parameter of media contained in the reactor interior 7 can be inserted into the receiving channel 8 and can be connected reversibly to the sensor adapter 3.

Figure 2:
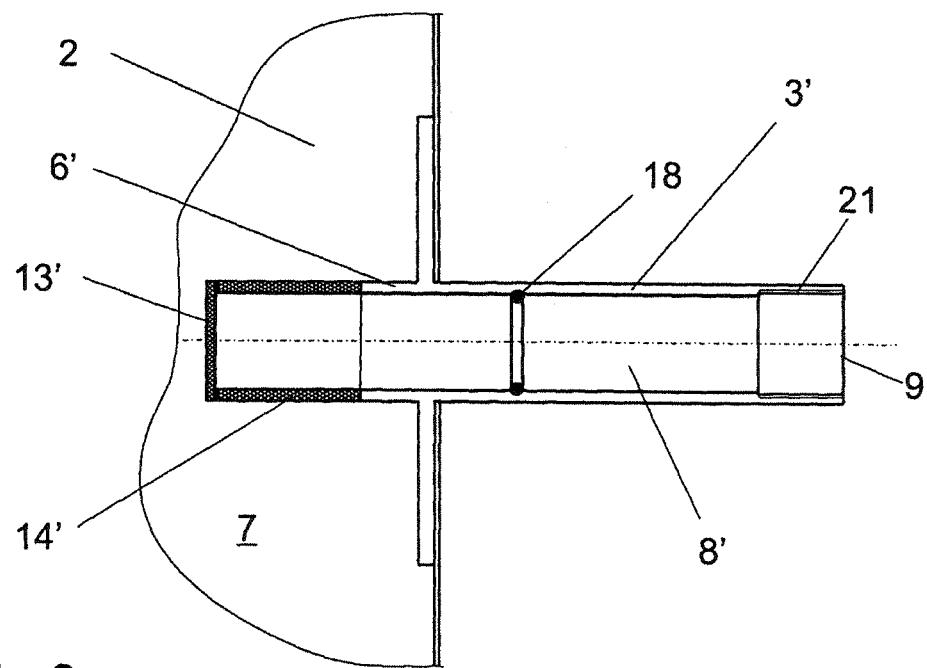
FIG. 2 shows a side view in section and in outline of a further container having a sensor adapter.
Figure 3:
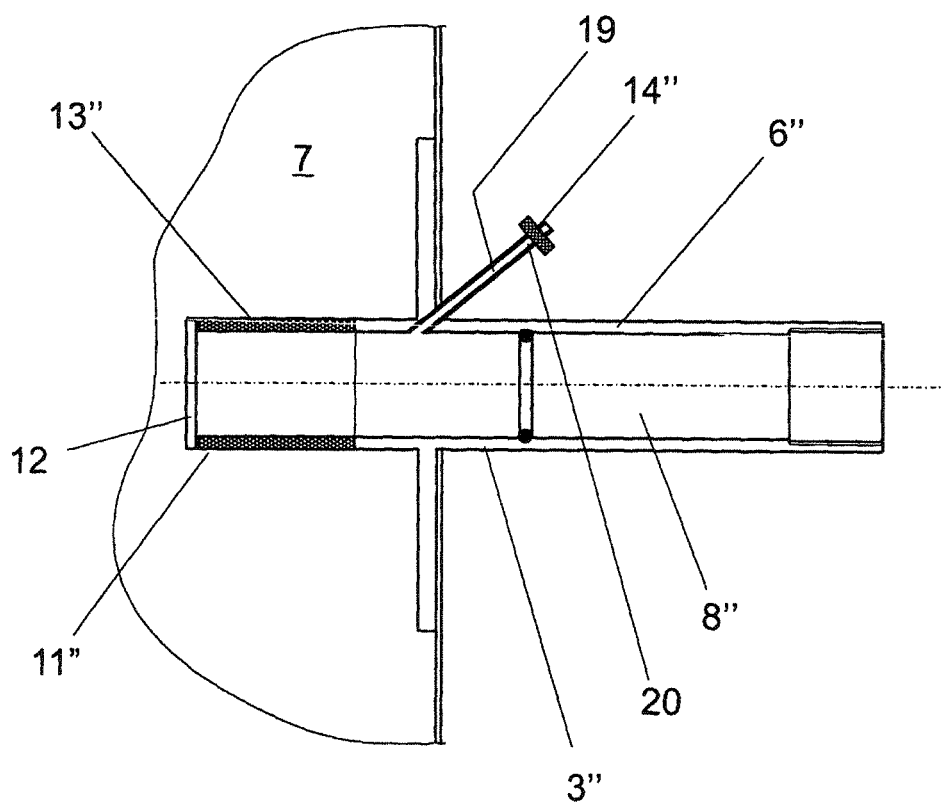
FIG. 3 shows a side view in section and in outline of a further container having a sensor adapter and a side channel leading outward.

In accordance with the embodiments in FIGS. 1 to 3, the container-side end 11 of the adapter shaft 3 projects into the reactor interior 7.

In accordance with the exemplary embodiment in FIG. 1, the end side of the container-side end 11 of the adapter shaft 6 is closed by a cover 12, which may be formed in a transparent manner. Toward the cover 12, the adapter shaft 6 or the receiving channel 8 has a first membrane 13. Next to the first membrane 13 in the direction of the flange 5, the receiving channel 8 or the container-side end 11 of the adapter shaft 6 has a second membrane 14. The membranes 13, 14, which are made of a polymer, have a pore size of ≤0.2 μm, in order to form a sterile barrier between the reactor interior 7 and the receiving channel 8. The sensor arrangement 10 inserted into the receiving channel 8 has sensors 15, 16 assigned to the membranes 13, 14. At its end 17 having the receiving opening 9, the receiving channel 8 or the adapter shaft 6 has a thread 21 for fastening the sensor arrangement 10. The wall of the receiving channel 8 has a sealing ring 18 for sealing off and guiding the sensor arrangement 10.

In accordance with the exemplary embodiment in FIG. 2, the adapter shaft 6' of the sensor adapter 3' has the first membrane 13' on its end side facing the reactor interior 7 and has the second membrane 14' adjacent thereto on the perimeter of the receiving channel 8.

In accordance with the exemplary embodiment in FIG. 3, the adapter shaft 6" of the sensor adapter 3" has the first membrane 13" at its container-side end 11". At its end-side end, the receiving channel 8" is closed by the cover 12. The adapter shaft 6" has a side channel 19, which leads outward from the receiving channel 8" and the access opening 20 of which, which is located outside the container interior, is covered by a second membrane 14".

Figure 4:
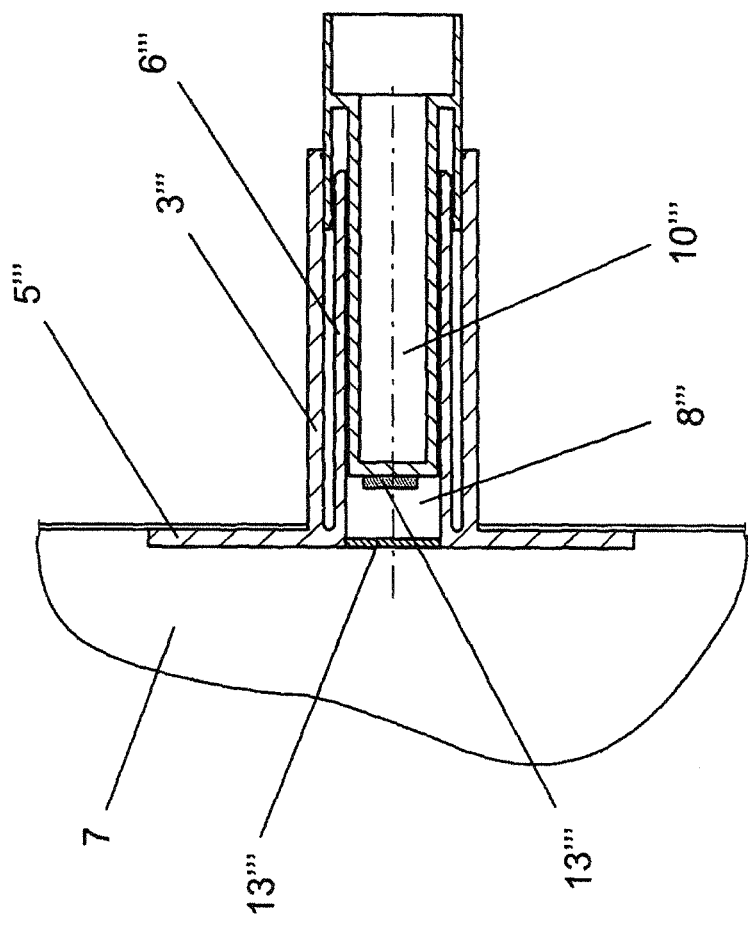
FIG. 4 shows a side view in section and in outline of a further container having a sensor adapter and a sensor arrangement.

In accordance with the embodiment in FIG. 4, the receiving channel 8''' of the sensor adapter 3''' ends toward the reactor interior 7 in the flange 5''', its container-side opening being covered by a first membrane 13'''. In the receiving channel 3''', the sensor arrangement 10''' is guided in the form of a plunger and is arranged such that it can be moved longitudinally.

Figure 5:
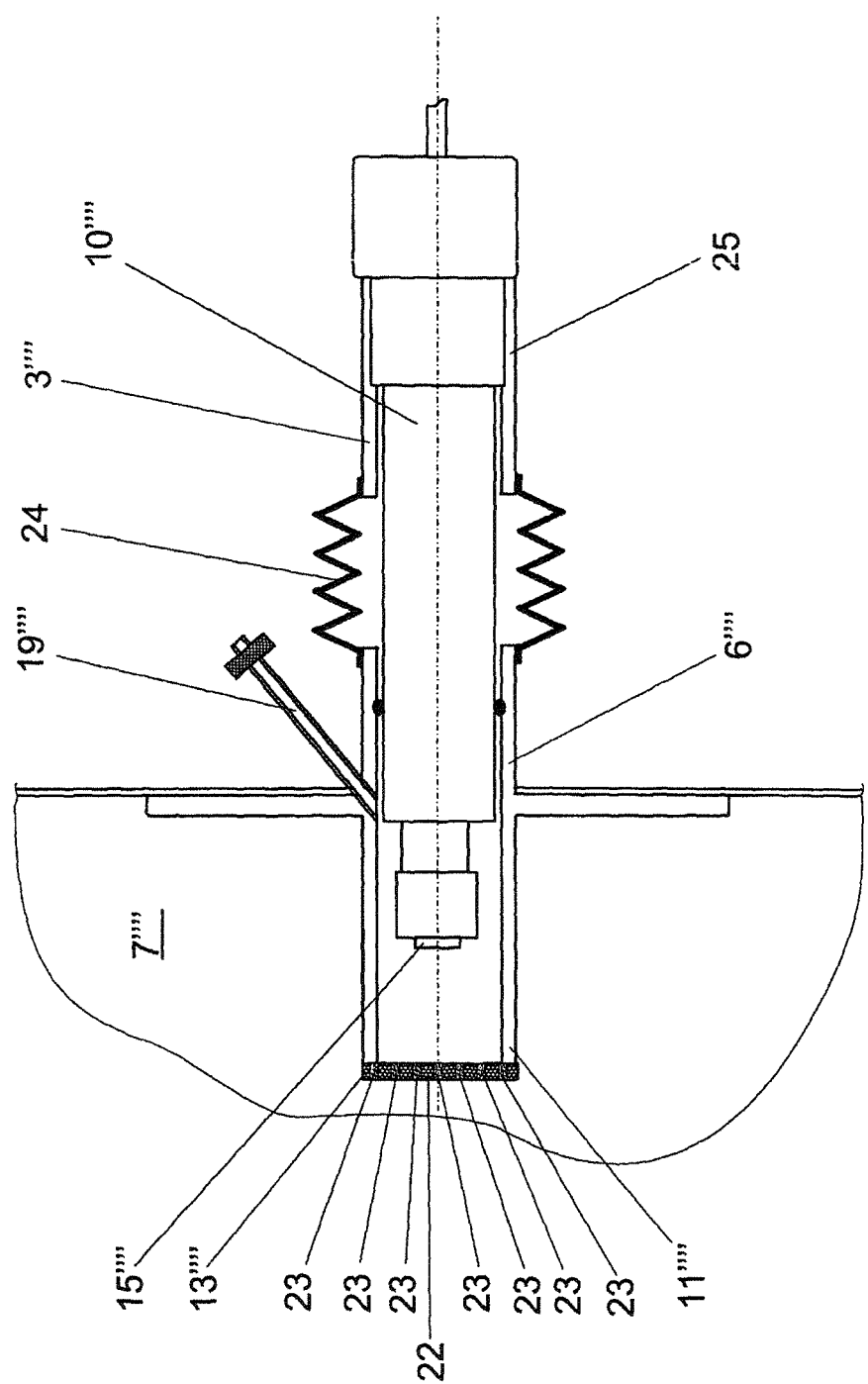
FIG. 5 shows a side view in section and in outline of a further container having a sensor adapter, a side channel leading outward and a membrane having different regions.

In accordance with the exemplary embodiment in FIG. 5, the adapter shaft 6'''' of the sensor adapter 3'''' has the membrane 13'''' at its container-side end 11''''. The membrane 13'''' has a region 22 having hydrophilic properties which is interspersed with spots or regions 23 which form small islands and have hydrophobic properties.

At its end remote from the membrane 13'''', the receiving channel 8'''' has an adapter attachment 25 for coupling the sensor arrangement 10''''. The adapter attachment 25 is connected to the adapter shaft 6'''' via a bellows 24, so that the sensor arrangement 10'''' can be moved longitudinally in the receiving channel 8'''' of the adapter shaft 6''''. The adapter shaft 6'''' has a side channel 19'''', which leads outward from the receiving channel 8'''' and the access opening 20'''' of which, which is located outside the container interior 7'''', is covered by a second membrane 14''''.

When the sensor arrangement 10'''' is advanced in the direction of the membrane 13'''', gas received via the side channel 19'''' can be pressed in a sterile manner via the hydrophobic regions 23 into the container interior 7''''. Hydrophilic medium from the container interior 7'''' can penetrate into the receiving channel 8'''' and flow around the sensor 15'''' of the sensor arrangement 10''''.

The invention claimed is:

1. A container (2) comprising: a wall (4) defining a container interior (7) for containing a medium or media therein, a sensor adapter (3) having a flange (5) secured to the wall (4) and a receiving channel (8, 8", 8''') extending from the flange (5) and configured for reversibly receiving a sensor arrangement (10, 10''', 10'''') for measuring at least one parameter of the medium or media contained in the container interior (7), the receiving channel (8, 8'', 8''') having an externally accessible receiving opening (9) and having an inner end communicating with the medium or media in the container interior (7), at least one seal (18) in the receiving channel (8, 8'', 8''') for providing sealing between the receiving channel (8, 8'', 8''') and the sensor arrangement (10, 10''', 10'''') when the sensor arrangement (10, 10''', 10'''') is reversibly received in the receiving channel (8, 8'', 8'''), at least one area of the receiving channel (8, 8'', 8''') adjacent the inner end having at least one boundary surface formed by a membrane (13, 13', 13'', 13''', 13'''', 14, 14', 14'') between the medium or media in the container interior and the sensor arrangement (10, 10''', 10'''') and via which the medium or media to be measured can be supplied directly to the sensor arrangement (10, 10''', 10''''), while preventing contamination of the container interior (7) and the medium or media therein from the receiving channel (8, 8'', 8''') or the sensor arrangement (10, 10''', 10'''') in the receiving channel.

2. The container as claimed in claim 1, characterized in that the membrane (13, 13', 13'', 13''', 13'''', 14, 14', 14'') has a pore size of between 0.1 and 0.4 µm.

3. The container as claimed in claim 2, characterized in that the membrane (13, 13', 13'', 13''', 13'''', 14, 14', 14'') has a pore size of ≤0.2 µm and forms a sterile barrier.

4. The container as claimed in claim 1, characterized in that the membrane (13, 13', 13'', 13''', 14, 14', 14'') has hydrophilic or hydrophobic or oleophobic properties.

5. The container as claimed in claim 1, characterized in that the membrane (13'''') has one or more regions (22) having hydrophilic properties and one or more regions (23) having hydrophobic properties.

6. The container as claimed in claim 1, characterized in that the membrane (13, 13', 13'', 13''', 13'''', 14, 14', 14'') is made from a natural polymer.

7. The container as claimed in claim 6, characterized in that the membrane (13, 13', 13'', 13''', 13'''', 14, 14', 14'') is made from cellulose acetate or regenerated cellulose.

8. The container as claimed in claim 1, characterized in that the membrane (13, 13', 13'', 13''', 13'''', 14, 14', 14'') is made from a synthetic polymer.

9. The container as claimed in claim 8, characterized in that the membrane (13, 13', 13'', 13''', 13'''', 14, 14', 14'') is made from polysulfone.

10. The container as claimed in claim 1, characterized in that the receiving channel (8) forms an adapter shaft (6) projecting into the container interior (7), said adapter shaft (6) having two successively arranged membranes (13, 14) that have different properties, and having a closed end 12.

11. The container as claimed in claim 1, characterized in that the receiving channel (8') forms an adapter shaft (6') projecting into the container interior (7), said adapter shaft (6') having a first membrane (13') that closes an end of the adapter shaft (6') in the container interior (7), and having a second membrane (14') arranged on a perimeter of the adapter shaft (6') and has different properties than the first membrane (13').

12. The container as claimed in claim 1, characterized in that the receiving channel (8'') forms an adapter shaft (6'') projecting into the container interior (7), said adapter shaft (6'') having a first membrane (13'') arranged on the perimeter of the adapter shaft (6''), the adapter shaft (6'') having a closed end and having a side channel (19) that leads outward and has an access opening (20) located outside the container interior (7), the access opening (20) being covered by a second membrane (14'').

13. The container as claimed in claim 1, characterized in that the sensor arrangement (10''') is arranged in the form of a plunger in the receiving channel (8''') such that it can be moved longitudinally in order to generate a pressure.

14. The container as claimed in claim 1, characterized in that the sensor arrangement (10'''') is arranged such that it can be moved longitudinally in the receiving channel (8'''') by way of a bellows (24) that is part of the adapter.

15. The container as claimed in claim 1, characterized in that the sensor adapter (3, 3', 3'', 3''', 3'''') consists of a material that is resistant to at least one of beta radiation, gamma radiation and ETO.

16. The container as claimed in claim 1, characterized in that the container (2) is in the form of a disposable bioreactor (1).

17. The container as claimed in claim 16, wherein at least part of the at least one membrane (13, 13', 13'', 13''', 13'''', 14, 14', 14'') is spaced from both the wall of the container (2) and an end of the receiving channel (8, 8'', 8''').

\* \* \* \* \*